United States Patent [19]
Breach

[11] Patent Number: 5,858,304
[45] Date of Patent: Jan. 12, 1999

[54] VACUUM JACKETED STEAM STERILIZER

[75] Inventor: Michael R. Breach, Erie, Pa.

[73] Assignee: Steris Corporation, Mentor, Ohio

[21] Appl. No.: 783,504

[22] Filed: Jan. 14, 1997

[51] Int. Cl.⁶ ................................................. A61L 2/08
[52] U.S. Cl. .............................. 422/26; 422/1; 422/297;
422/300
[58] Field of Search ........................... 422/26, 1, 297,
422/300

[56] References Cited

U.S. PATENT DOCUMENTS

| | | | |
|---|---|---|---|
| 3,961,893 | 6/1976 | Russell et al. ............................... | 21/95 |
| 4,111,654 | 9/1978 | Fahlvik et al. ............................ | 422/26 |
| 4,263,258 | 4/1981 | Kalasek ..................................... | 422/113 |
| 4,723,410 | 2/1988 | Otters ........................................ | 60/518 |
| 4,859,423 | 8/1989 | Perlman ................................... | 422/102 |
| 4,944,919 | 7/1990 | Powell ..................................... | 422/26 |
| 5,026,524 | 6/1991 | Powell et al. ............................. | 422/26 |
| 5,122,344 | 6/1992 | Schmoegner ............................. | 422/111 |
| 5,223,229 | 6/1993 | Brucker .................................... | 422/116 |
| 5,316,171 | 5/1994 | Danner, Jr. et al. ..................... | 220/423 |
| 5,652,550 | 7/1997 | Vig ............................................ | 331/68 |

Primary Examiner—Krisanne Thornton
Attorney, Agent, or Firm—Fay, Sharpe, Beall, Fagan, Minnich & McKee

[57] ABSTRACT

A pressure vessel (12) has a chamber (10) closed by a door (14). Steam, from a steam source (38) is selectively supplied to the interior of the pressure vessel to sterilize received items. The pressure vessel has an electric heater (24) for a steam passage or jacket (50) extending circumferentially therearound to heat the pressure vessel wall above the saturation temperature to prevent condensation within the pressure vessel. A vacuum jacket (20) surrounds the pressure vessel and the heater to provide an annular vacuum insulation region. A vacuum pump (30) is operated, as necessary, to maintain the vacuum between the vacuum jacket and the pressure vessel and is utilized when appropriate to draw a vacuum within the pressure vessel (12).

15 Claims, 2 Drawing Sheets

VACUUM JACKETED STEAM STERILIZER

BACKGROUND OF THE INVENTION

The present invention relates to the sterilization arts. It finds particular application in conjunction with steam sterilizers for medical, dental, and surgical equipment and will be discussed with particular reference thereto. It is to be appreciated, however, that the invention is also applicable to other high temperature sterilization and decontamination techniques.

Traditionally, steam sterilizers are used for destroying the microorganisms that may be present on medical equipment. Effective sterilization is achieved by a combination of temperature, pressure and exposure time. The sterilizer inner surface and the items to be sterilized are heated to the "saturation temperature" corresponding to the temperature at which water stays in the vapor form at a given pressure. If the saturation temperature is not maintained throughout the sterilization vessel, condensation may occur, resulting in the formation of water droplets. When living microorganisms become suspended in water, the water shields them from the steam. Moreover, as the water droplets run or are absorbed by sterile wraps or parts of the sterilized items, the water can carry the microorganisms through the sterile wraps and otherwise on to the previously sterilized items.

To prevent condensation, the walls of the pressure vessel in a conventional steam sterilizer are surrounded by a steam jacket. The steam jacket maintains the temperature of the vessel walls at or above the saturation temperature. This heats the items and structures in the pressure vessel, as well as the walls of the vessel above the saturation temperature.

Typically, the steam jacket consists of a metallic enclosure, around the pressure vessel. The steam is passed through a channel between the pressure vessel and the jacket walls. Heat from the steam is conducted through the walls of the pressure vessel, establishing and maintaining the temperature within the pressure vessel. Without such steam heating through the jacket, the metallic walls of the pressure vessel and the inner structures would be below the saturation temperature when steam is introduced to the pressure vessel.

Although the steam jacket is an effective way to heat the pressure vessel, such double walled pressure vessels are expensive to manufacture. Moreover, generating the steam to fill the jacket is expensive in energy, equipment, and time. The present invention provides a new and improved pressure vessel heating system which overcomes the above referenced problems and others.

SUMMARY OF THE INVENTION

In accordance with one aspect of the present invention, a sterilization apparatus is provided. A pressure vessel defines a chamber for receiving items to be sterilized. The pressure vessel has an inner surface and an outer surface and at least one opening for introducing and removing the items. A door selectively closes the pressure vessel opening. A vacuum jacket surrounds the pressure vessel. The vacuum jacket and pressure vessel outer surface define an enclosed annular space therebetween. A vacuum source evacuates the enclosed annular space. A heater heats the pressure vessel.

In accordance with another aspect of the present invention, a method of sterilization is provided. A vacuum is drawn in an annular region between a pressure vessel and vacuum jacket. Items to be sterilized are placed in the pressure vessel and a door to the pressure vessel closed. The pressure vessel is heated above a saturation temperature. The interior of the pressure vessel is evacuated. The vacuum within the pressure vessel is released and the pressure vessel is filled with steam. The interior of the pressure vessel is evacuated to remove the steam. The door is opened and the items are removed.

One advantage of the present invention is that it reduces the energy requirements.

Another advantage of the present invention is that it reduces material and manufacturing costs. A wider choice of materials including less costly materials are available.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
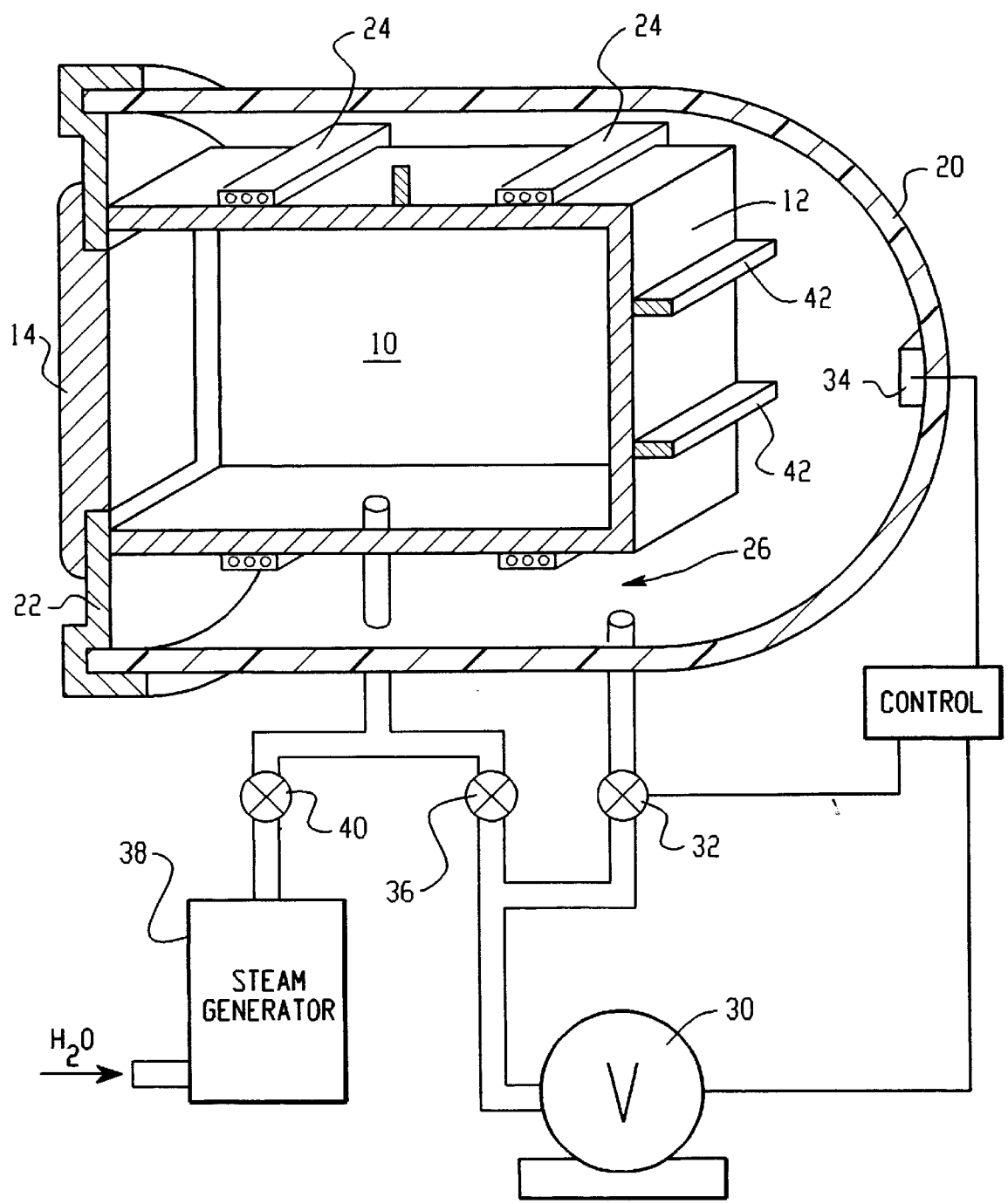
FIG. 1 is a cross-section of a vacuum enclosed steam sterilizer in accordance with the present invention.

With reference to FIG. 1, items to be sterilized are placed inside the sterilization region 10 surrounded by a stainless steel pressure vessel 12. A door 14 is closed to seal the pressure vessel during a steam sterilization cycle.

A cylindrical vacuum jacket 20 surrounds the pressure vessel 12 and is spaced therefrom. An end ring 22 seals an open end of the cylindrical jacket to an end of the pressured vessel 12 adjacent the door 14. The jacket 20 is preferably constructed of plastic, although other materials which are strong under compression and thermally insulative are also contemplated. A warm up heater 24 is wrapped around the pressure vessel 12. Preferably, the warm up heater is an electrical resistance heater for ease of control, although other heating mechanisms are also contemplated.

A vacuum pump 30 is connected with a space 26 between the pressure vessel 12 and the jacket 20. The vacuum pump draws a vacuum between the pressure vessel and the jacket to reduce thermal conductivity. A valve 32 is opened either periodically to assure that the vacuum is maintained, or when a vacuum sensor 34 indicates that the vacuum within the region is weakening. The vacuum pump 30 is also connected by a valve 36 to the sterilization chamber 10. A steam generator 38 is also connected by a steam control valve 40 with the sterilization chamber of the pressure vessel 12.

In operation, the vacuum pump 30 and valve 32 are actuated to draw a vacuum between the jacket and the pressure vessel. The warm up heater 24 is operated to heat the pressure vessel and its contents above the saturation temperature. The valve 36 connects the vacuum pump with the interior of the pressure vessel to evacuate the sterilization chamber 10. Drawing a vacuum within the pressure vessel when the items are heated helps to volatize water or other liquids which might be present on the items or in the chamber. After the evacuation cycle, the vacuum within the pressure vessel is released. The steam generator 38 fills the vacuum vessel with steam and raises the internal pressure above atmospheric pressure. Continued heating from the warm up heater 24 assures that the pressure vessel and its contents remain at or above the saturation temperature. At the end of a sterilization cycle, the steam control valve 40 is closed and the vacuum pump 30 and vacuum valve 36 are again actuated to drain and evacuate the steam from the pressure vessel. The vacuum pump continues to evacuate the pressure vessel during a drying time to be sure that all moisture has been removed from the pressure vessel and the items to be sterilized.

In the illustrated rectangular pressure vessel embodiment, strengthening ribs 42 are provided to keep planar wall sections of the pressure vessel from deflecting.

Figure 2:
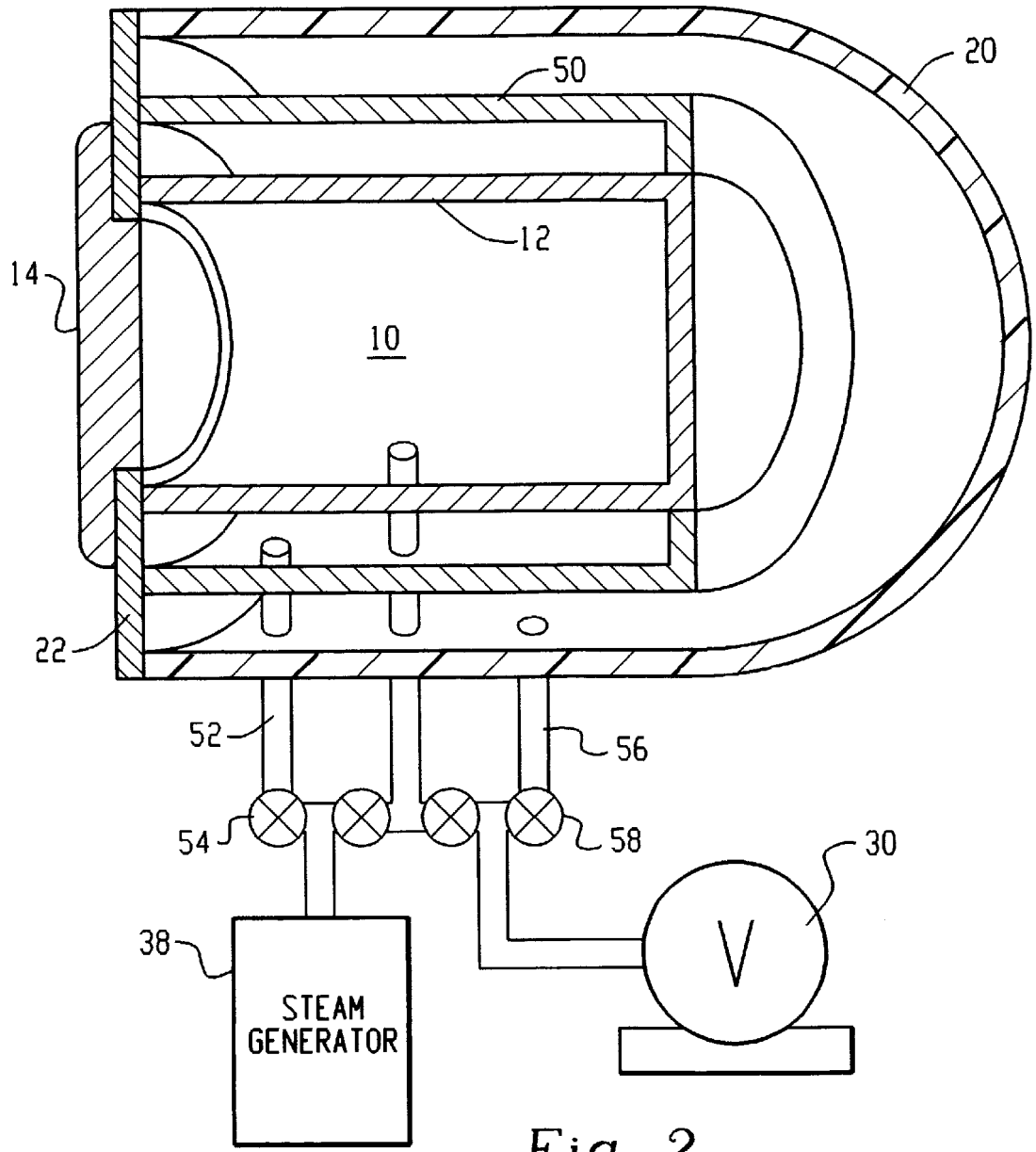
FIG. 2 is a cross-section of an alternate embodiment of a steam sterilizer.

With reference to FIG. 2, a steam passage for jacket 50 surrounds all or a portion of the pressure vessel 12. The vacuum jacket 20 surrounds the steam passage. In the illustrated embodiment, a pipe 52 passes through the vacuum enclosure. When a steam valve 54 is opened, the pipe introduces steam to the steam passage. A vacuum pipe 56 and valve 58 selectively remove spent steam from the vacuum enclosure. In this embodiment, the steam jacket acts as a warm-up heater. The vacuum jacket serves to reduce heat loss from the steam sterilizer and to maintain the temperature within the pressure vessel with little or no added energy.

Figure 3:
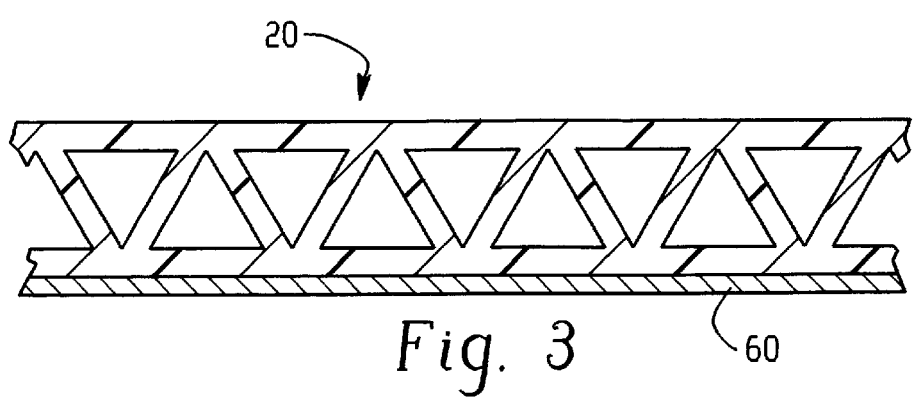
FIG. 3 is a cross-section of an enlarged portion of the vacuum jacket of FIG. 1.

With reference to FIG. 3, the vacuum jacket 20 has a honeycomb structure to increase its rigidity. A reflective layer 60 is provided on the inside surface of the vacuum jacket 20 to reduce radiant heat loss.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A sterilization apparatus comprising:
   (a) a pressure vessel defining a chamber for receiving items to be sterilized, the pressure vessel having an inner surface and an outer surface and at least one opening for introducing and removing the items;
   (b) a door for selectively closing the pressure vessel opening;
   (c) an insulation jacket surrounding the pressure vessel, the insulation jacket and the pressure vessel outer surface defining an enclosed annular space therebetween;
   (d) a steam source for injecting steam into the pressure vessel:
   (e) a vacuum source for selectively evacuating (1) the pressure vessel and (2) the enclosed annular space to form an evacuated annular space and for holding the annular space at vacuum such that the evacuated annular space serves as vacuum insulation for limiting heat loss from the pressure vessel while the pressure vessel is held at or above atmospheric pressure;
   (f) a heater which heats the pressure vessel; and,
   (g) a control for controlling the steam source and the vacuum source such that steam is injected into the pressure vessel concurrently with holding the annular space evacuated.

2. A sterilization apparatus comprising:
   (a) a pressure vessel defining a chamber for receiving items to be sterilized, the pressure vessel having an inner surface and an outer surface and at least one opening for introducing and removing the items;
   (b) a door for selectively closing the pressure vessel opening;
   (c) a steam source;
   (d) a vacuum jacket surrounding the pressure vessel, the vacuum jacket and the pressure vessel outer surface defining an enclosed annular space therebetween, the vacuum jacket being constructed of a non-metallic material;
   (e) a vacuum source for evacuating the enclosed annular space to draw a vacuum in the annular space putting a compressive load on the vacuum jacket;
   (f) a steam valve for selectively conveying steam from the steam source to the pressure vessel;
   (g) a first vacuum valve for selectively connecting the pressure vessel with the vacuum source;
   (h) a second vacuum valve for selectively connecting the vacuum jacket with the vacuum source, the first and second vacuum valves being independently operable, whereby the steam valve and the second vacuum valve are openable concurrently while the first vacuum valve is closed to maintain the vacuum in the vacuum jacket while supplying steam to the pressure vessel.

3. The apparatus as set forth in claim 1, wherein the insulation jacket is formed of a honeycomb structure to improve the rigidity of the jacket under vacuum.

4. A sterilization apparatus comprising:
   (a) a pressure vessel defining a chamber for receiving items to be sterilized, the pressure vessel having an inner surface and an outer surface and at least one opening for introducing and removing the items;
   (b) a door for selectively closing the pressure vessel opening;
   (c) a vacuum jacket surrounding the pressure vessel, the vacuum jacket and the pressure vessel outer surface defining an enclosed annular vacuum space therebetween;
   (d) a vacuum source for evacuating the enclosed annular space;
   (e) a heater which heats the pressure vessel, the heater including a steam passage, the vacuum jacket and the annular vacuum space surrounding both said steam passage and said pressure vessel;
   (f) a steam source which is controllable to supply steam to the pressure vessel and the heater steam passage;
   (g) a vacuum source which is intermittently connectable to (1) the pressure vessel and the heater steam passage to eject steam therefrom and (2) the vacuum jacket to maintain a steam-free vacuum therein, which vacuum limits a transfer of heat across the vacuum jacket.

5. The apparatus as set forth in claim 1, wherein the heater includes a resistive heating coil.

6. The apparatus as set forth in claim 1, further including valves and tubing for selectively connecting the vacuum source with the chamber and the enclosed annular space.

7. A sterilization apparatus comprising:
   (a) a pressure vessel defining a chamber for receiving items to be sterilized, the Pressure vessel having an inner surface and an outer surface and at least one opening for introducing and removing the items;

(b) a door for selectively closing the pressure vessel opening;

(c) a vacuum jacket surrounding the pressure vessel, the vacuum Jacket and the pressure vessel outer surface defining an enclosed annular space therebetween;

(d) a vacuum source for drawing and maintaining the enclosed annular space to a vacuum: and (e) a heat reflective coating on the vacuum jacket to reduce heat loss.

8. A steam sterilizer including a metal pressure vessel, a door for selectively providing access to an interior of the pressure vessel for introducing items to be sterilized, a source of steam connected with the interior of the pressure vessel for selectively introducing sterilizing steam, and a vacuum pump connected with the interior of the pressure vessel for selectively evacuating the interior of the pressure vessel, and further including:

a vacuum insulation jacket disposed surrounding and displaced from the pressure vessel to reduce heat loss from the pressure vessel and to maintain the temperature within the pressure vessel;

a valve for selectively connecting the vacuum pump with a region between the pressure vessel and the vacuum jacket for drawing and maintaining a vacuum therein;

a vacuum sensor for sensing a vacuum level in the vacuum jacket; and, a control connected with the vacuum sensor and the valve to open and close the valve such that a preselected vacuum level is drawn and maintained in the vacuum jacket.

9. The steam sterilizer as set forth in claim 8, further including a heater for heating the pressure vessel.

10. A method of sterilization comprising:

evacuating an enclosed annular region between a pressure vessel and a vacuum jacket to draw the annular region to a vacuum;

placing items to be sterilized within an interior chamber of the pressure vessel;

heating the pressure vessel;

drawing a vacuum within the pressure vessel;

introducing steam into the interior of the pressure vessel without introducing steam into the enclosed annular region;

maintaining the vacuum within the enclosed annular region to create a vacuum insulator for the pressure vessel;

applying a vacuum to the interior of the pressure vessel to pull out the steam;

removing the items from the interior of the pressure vessel.

11. The sterilization method as set forth in claim 10, wherein the heating step includes:

heating the pressure vessel with an electric resistance heater.

12. The sterilization method as set forth in claim 10, wherein the heating step includes:

heating the pressure vessel with steam.

13. A sterilization method comprising:

(a) placing items to be sterilized within an interior chamber of a pressure vessel;

(b) heating the pressure vessel;

(c) drawing a vacuum within the pressure vessel;

(d) introducing steam into the interior of the pressure vessel;

(e) holding the steam in the interior of the pressure vessel for a selected duration;

(f) applying a vacuum to the interior of the pressure vessel to pull out the steam;

(g) thermally insulating the pressure vessel during steps (b)–(f), by selectively actuating a vacuum pump and valve to draw and maintain a preselected vacuum level in an enclosed annular region between the pressure vessel and a vacuum jacket;

(h) monitoring the vacuum between the vacuum jacket and the pressure vessel; and, (i) removing the items from the interior of the pressure vessel.

14. The sterilization method as set forth in claim 10, wherein in the heating step, the pressure vessel is heated above a saturation temperature for water.

15. The sterilization method as set forth in claim 10, further including reflecting radiant heat energy which reaches the vacuum jacket back toward the pressure vessel.

* * * * *